United States Patent [19]

Brechbühler et al.

[11] 4,225,598

[45] Sep. 30, 1980

[54] 2-CYCLOPROPYLAMINO-4,6-DIAMINO-S-TRIAZINE

[75] Inventors: Hans U. Brechbühler, Basel, Switzerland; Verena Laanio, Arisdorf; Dagmar Berrer, Riehen, both of Fed. Rep. of Germany

[73] Assignee: Ciba-Geigy Corporation, Ardsley, N.Y.

[21] Appl. No.: 962,839

[22] Filed: Nov. 21, 1978

Related U.S. Application Data

[63] Continuation-in-part of Ser. No. 869,990, Jan. 16, 1978, abandoned, which is a continuation-in-part of Ser. No. 824,667, Aug. 15, 1977, abandoned.

[30] Foreign Application Priority Data

Aug. 19, 1976 [CH] Switzerland ................... 10558/76

[51] Int. Cl.² .................... C07D 251/70; A01N 9/22

[52] U.S. Cl. .................................. 424/249; 544/197
[58] Field of Search ..................... 544/197; 424/249

[56] References Cited

U.S. PATENT DOCUMENTS

| | | | |
|---|---|---|---|
| 2,567,847 | 9/1951 | Kaiser | 544/113 |
| 2,742,466 | 4/1956 | Randall | 544/197 |
| 2,909,421 | 10/1959 | Gysin et al. | 544/197 |
| 3,853,868 | 12/1974 | Herzog et al. | 544/197 |

FOREIGN PATENT DOCUMENTS 483163  5/1952  Canada ................................ 544/197

*Primary Examiner*—John M. Ford
*Attorney, Agent, or Firm*—Harry Falber

[57] ABSTRACT

2-Cyclopropylamino-4,6-diamino-s-triazine and acid addition salts thereof for combatting developmental stages of insects.

6 Claims, No Drawings

2-CYCLOPROPYLAMINO-4,6-DIAMINO-S-TRIAZINE

CROSS REFERENCE TO RELATED APPLICATIONS

This is a continuation-in-part of application Ser. No. 869,990 filed Jan. 16, 1978, now abandoned which is in turn a continuation-in-part of application Ser. No. 824,667 filed Aug. 15, 1977, now abandoned.

DETAILED DISCLOSURE

The present invention relates to the novel compound 2-cyclopropylamino-4,6-diamino-s-triazine of the formula

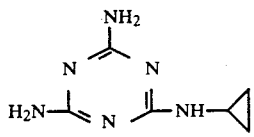

and acid addition salts thereof, and to their use in pest control.

The term "acid addition salts" of 2-cyclopropylamino-4,6-diamino-s-triazine is to be understood as meaning salts with strong mineral acids, for example salts with hydrochloric acid or sulphuric acid.

2-Cyclopropylamino-4,6-diamino-s-triazine is obtained by methods which are known per se, for example by (a) reacting a 2-cyclopropylamino-4-amino-6-halogeno-s-triazine in which halogen preferably is chlorine, with ammonia or (b) reacting a 2,4-diamino-6-halogeno-s-triazine in which halogen preferably is chlorine, with cyclopropylamine or (c) reacting a 2-cyclopropylamino-4,6-dihalogeno-s-triazine in which halogen preferably is chlorine, with ammonia.

The substitution of the halogen atoms with ammonia or cyclopropylamine is effected by dissolving the triazine derivatives used as starting materials as defined under (a), (b), and (c), in inert solvents, for example acetone, acetone/water mixtures, methyl ethyl ketone, dioxane or dioxane/water mixtures, and reacting these mixtures at normal or, if appropriate, elevated pressure and at temperatures between 20° and 150° C., preferably between 50° and 140° C., with ammonia or cyclopropylamine. The 2-cyclopropylamino-4,6-diamino-s-triazine obtained melts at 219°–222° C.

Most of the triazine derivatives used as starting materials are known or they can be obtained in accordance with known methods.

Diamino- and triamino-s-triazines are described as chemosterilants for adult houseflies (*Musca domestica*) in U.S. Pat. No. 3,189,521. The chemosterilising action on insects of 2,4,6-triamino-s-triazine derivatives (melamine derivatives) is also described by S. Nagasawa et al., Botyu-Kagaku 39 (4), 105 (1974). A. B. Borkovec and A. B. DeMilo [J. Med. Chem. 10 (5), 457 (1967)] and G. G. LaBrecque, R. L. Fye, A. B. DeMilo and A. B. Borkovec [J. Econ. Entomol. 61, (6) 1621 (1968)] also describe the chemosterilising action of, among other compounds, 2-cyclohexylamino-4,6-diamino-s-triazine, 2-cyclohexylamino-4,6-dihexylamino-s-triazine and 2,4,6-tris-cyclohexylamino-s-triazine, and the salts thereof, on adult houseflies (*Musca domestica*).

The above mentioned insecticidal chemosterilants are employed to adult insects, i.e. the stage of reproduction and dissemination for impairing or preventing capability of producing offspring of said insects. Combatting populations of harmful insects by introduction of sterile insects capable of copulating into a normal insect population taking final aim at self-destruction represents an indirect method for combatting insects.

In practice, degeneration of an insect population by introduction of sterile insects into said population extends to a sequence of some to numerous generations of insects and therefore, further dissemination of organisms harmful to men or animals may occur by vector insects. Furtheron, insects may gradually become resistent to applied chemosterilants.

Therefore, direct methods for combatting insects by killing them or preventing individual development are required.

Surprisingly, it has now been found that treating insect larvae representing the stage of eating and growing with 2-cyclopropyl-amino-4,6-diamino-s-triazine or salts thereof results in killing the freshly hatched larvae or preventing adults from hatching from the pupae. The mode of action of 2-cyclopropylamino-4,6-diamino-s-triazine and salts thereof is not to be compared with that of classical insecticides, chemosterilants or juvenile hormone analogues.

2-Cyclopropylamino-4,6-diamino-s-triazine and salts thereof can be used in particular for controlling hygiene pests and animal ectoparasites of the order Diptera and of the families: Culicidae, Simuliidae, Tipulidae, Muscidae and Calliphoridae.

2-Cyclopropylamino-4,6-s-triazine and salts thereof can be used as pure active substance or together with suitable carriers and/or additives. Suitable carriers and additives can be solid or liquid and correspond to the substances conventionally used in the art of formulation, for example natural or regenerated substances, solvents and/or dispersants.

The compositions according to the invention are manufactured in known manner by homogeneously mixing and/or grinding the active substance with the suitable carriers, with or without the addition of dispersants or solvents which are inert to the active substance.

The active substance may be processed to the following formulations:

Solid formulations:
  Dusts, tracking agents and granules (coated granules, impregnated granules and homogeneous granules), premix (feed additive).

Liquid formulations:
  (a) active substance concentrates which are dispersible in water: wettable powders, pastes and emulsions;
  (b) solutions; sprays (aerosols).

To manufacture solid forms (dusts, tracking agents), the active substance is mixed with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

Granules can be very easily manufactured by dissolving the active substance in an organic solvent and applying the solution thereby obtained to a granulated mineral, for example attapulgite, $SiO_2$, granicalcium, bentonite etc. and then evaporating the solvent.

Polymer granules can also be manufactured by mixing the active substance with polymerisable compounds (urea/formaldehyde; dicyandiamide formaldehyde or others), whereupon a mild polymerisation is carried out that does not affect the active substance and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substance, for example in the form of their solutions (in a low boiling solvent) and to remove the solvent. Polymer granules of this kind in the form of microgranules having preferably a bulk density of 300 g/liter to 600 g/liter can also be manufactured with the aid of atomisers.

It is also possible to obtain granules by compacting the carrier with the active substance and additives and subsequently commminuting the product.

To these mixtures can also be added additives which stabilize the active substance and/or nonionics, anionics and cationics, which, for example, ensure a better wettability (wetting agents) and dispersibility (dispersants). Examples of suitable substances are: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, ligninsulphonic acid, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide, propylene oxide, polyvinylpyrrolidone, polyvinyl alcohol, condensation products of urea and formaldehyde, and also latex products.

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and anti-foams and, if appropriate, solvents.

Wettable powders and pastes are obtained by mixing and grinding the active substance with dispersants and pulverulent carriers in suitable devices until homogenity is attained. Suitable carriers are, for example, those already mentioned for the solid forms of application. In some cases it is advantageous to use mixtures of different carriers. Examples of dispersants are: condensation products of sulphonated naphthalene and sulphonated naphthalene derivatives with formaldehyde, condensation products of naphthalene or naphthalene sulphonic acids with phenol and formaldehyde, as well as alkali metal, ammonium and alkaline earth metal salts of ligninsulphonic acid, in addition alkylarylsulphonates, alkali metal and alkaline earth metal salts of dibutylnaphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyl-dilaurylammonium chloride and fatty acid alkali metal and alkaline earth metal salts.

Suitable anti-foams are for example silicone oils.

The active substance is so mixed, ground, sieved and strained with the additives mentioned above that, in wettable powders, the solid particle size of 0.02 to 0.04 mm and in pastes, of 0.03 mm, is not exceeded. Emulsifiable concentrates and pastes are manufactured by using dispersants, such as those referred to above, organic solvents, and water. Examples of suitable solvents are: alcohols, dimethyl sulphoxide, and mineral oil fractions which boil between 120° and 350° C. The solvents must be virtually odourless and inert to the active substances.

Furthermore, the compositions according to the invention can be applied in the form of solutions. For this purpose the active substance is dissolved in suitable organic solvents or mixtures of solvents. Aliphatic and aromatic hydrocarbons, chlorinated derivatives thereof, alkylnaphthalenes and mineral oils, singly or in admixture, can be used as organic solvents.

Formulations of the active substance are described hereinafter. The parts denote parts by weight.

Dusts

The following substances are used to manufacture (a) a 0.5% and (b) a 2% dust:

(a)

0.5 part of active substance
99.5 parts of talc (b)

2 parts of active substance
1 part of highly disperse silicic acid
97 parts of talc.

The active substances are mixed with the carriers and ground.

Tracking Agents 5 parts of active substance are mixed with
95 parts of carbonate of lime and ground to an average particle size of 80μ.

Granules 5 parts of active substance are dissolved in a solvent, e.g. methylene chloride, and mixed with 2 parts of polyethylene glycol ("Carbowax").
91.5 parts of calcium carbonate are impregnated with the mixture and
1.5 parts of precipitated silicic acid are admixed.
The solvent is subsequently evaporated.

Wettable Powder 50 parts of active substance are mixed with
5 parts of a dispersing agent, e.g. sodium ligninsulphonate,
5 parts of a wetting agent, e.g. dibutylnaphthalenesulphonic acid
10 parts of silicic acid and
30 parts of China clay
and the mixture is finely ground.

Emulsifiable Concentrate 20 parts of active substance are mixed with 20 parts of emulsifier, e.g. a mixture of alkylarylpolyglycol ether with alkylarylsulphonates, and
60 parts of solvent until the solution is completely homogeneous.

By diluting this concentrate with water it is possible to obtain an emulsion of the desired concentration.

Premix (feed additive)

0.25 part of active substance and
4.75 parts of secondary calcium phosphate, or China clay, aerosil or carbonate of lime are homogeneously mixed with
95 parts of an animal feed, e.g. poultry food.

Spray

The following constituents are used to manufacture a 2% spray:

2 parts of active substance
98 parts of kerosene.

Other biocidal active substances or agents can be admixed with the compositions described hereinabove. Thus in addition to 2-cyclopropylamino-4,6-diamino-s-triazine or salts thereof the compositions of the present invention can obtain, for example, insecticides to broaden the activity spectrum.

The compositions, or the active compounds contained therein, exert their inhibitory action therefore chiefly on the development of larvae or pupae of insects, preferably of the order Diptera.

EXAMPLE 1

2-Cyclopropylamino-4,6-diamino-s-triazine (a) 133 g of cyanuric chloride are suspended in 720 ml of chlorobenzene and cooled to $-10°$ C. To this suspension are added with stirring 50 ml of cyclopropylamine dropwise over a period of 25 minutes. Keeping the temperature at $-10°$ C., 96 ml of aqueous sodium hydroxide (30% NaOH) are added dropwise. The reaction mixture is then stirred at $-10°$ C. for 1½ hours and allowed to stand for a further 16 hours at room temperature, after which it is washed with water (2×400 ml), dried over anhydrous sodium sulphate and filtered. The excess chlorobenzene is then removed by water jet vacuum distillation. 138 g of 2-cyclopropylamino-4,6-dichloro-s-triazine in the form of white crystals are obtained.

Melting point: 99°–101° C.

(b) 138 g of 2-cyclopropylamino-4,6-dichloro-s-triazine are added at a slightly elevated tmeperature and with vigorous stirring to a mixture of 675 ml of dioxane and 135 ml of ether. After cooling to room temperature, 101 ml of 25%, aqueous ammonia are added dropwise over a period of 20 minutes. The reaction mixture is heated to 50° C., stirred for 16 hours and then concentrated by evaporation under water jet vaccum. The dry riesidue is diluted with 500 ml. of water and after stirring for 1 hour at room temperature, the tiny white crystals formed are separated by filtering under suction and dried under water jet vacuum at 80° C. 217 g. of 2-cyclopropylamino-4-chloro-6-amino-s-triazine are obtained.

Melting point 188°–189° C.

(c) A mixture of 100 g of 2-cyclopropylamino-4-chloro-6-amino-s-triazine, 51 g of anhydrous ammonia and 500 ml of dioxane is heated for 24 hours in an autoclave at 140° C. After cooling to room temperature the solvent is removed by water jet vacuum distillation. 300 ml of water are added to the residue. After stirring, the residue product is filtered off and recrystallised from boiling ethanol. 50 g of 2-cyclopropylamino-4,6-diamino-s-triazine are obtained. Melting point: 219°–222° C.

EXAMPLE 2

2-Cyclopropylamino-4,6-diamino-s-triazine dihydrochloride 25 g of 2-cyclopropylamino-4,6-diamino-s-triazine are dissolved in 2000 ml of boiling abs. ethanol and the clear, colorless solution obtained is cooled to 15° C. Under further cooling with ice water, dry, gaseous hydrogen chloride is introduced until the solution is saturated. The precipitated white crystals are filtered off by suction and washed with abs. ether. 32 g of 2-cyclopropylamino-4,6-diamino-s-triazine dihydrochloride are obtained. Melting point: 195° C. under decomposition (separation of HCl).

EXAMPLE 3

2-Cyclopropylamino-4,6-diamino-s-triazine monochloride monohydrate

2-Cyclopropylamino-4,6-diamino-s-triazine is added to boiling 10% aqueous hydrochloric acid until the latter is almost saturated. After cooling to room temperature, 2-cyclopropylamino-4,6-diamino-s-triazine monohydrochloride monohydrate in the form of crystals is obtained.

Melting point: 235°–237° C. under decomposition.

EXAMPLE 4

Test substance: 2-Cyclopropylamino-4,6-diamino-s-triazine or an acid addition salt thereof formulated as acetonic solutions Test subject: Musca domestica Test material: CSMA nutrient substrate for maggots Concentration: 0.1%, 0.05%, 0.01% of active substance Test method:

50 g of freshly prepared CSMA nutrient substrate for maggots are charged into beakers. A specific amount of a 1% acetonic solution of the respective active substance is pipetted onto the nutrient substrate present in the beakers. The substrate is then thoroughly mixed and the acetone subsequently allowed to evaporate over a period of at least 20 hours.

Then 25 one-day-old maggots of Musca domestica are put into each of the beakers containing the treated nutrient substrate for testing with each active substance at one of its given concentrations. After 5 days, the pupae are separated from the substrate by flushing them out with water and then deposited in the same beaker.

Each batch of flushed out pupae is counted to determine the toxic effect of the active substance on the maggot development. The number of flies which have hatched out of the pupae are then counted after 10 days and any influence on the metamorphosis thereby determined.

2-Cyclopropylamino-4,6-diamino-s-triazine and acid addition salts thereof exhibit good activity in this test.

EXAMPLE 5

Test substance: 2-cyclopropylamino-4,6-diamino-s-triazine or an acid addition salt thereof formulated as acetonic solutions.

Test subject: Aëdes aegypti

Test material: yoghourt beakers filled with water

Concentration: 10 ppm, 5 ppm, and 1 ppm of active substance

Test method:

Yoghourt beakers are each filled with 150 ml of water and a specific amount of a 0.1% solution of the active substance in acetone is pipetted onto the surface of the water. After the acetone has evaporated, 30 to 40 two-day-old larvae of Aëdes aegypti are put into each of the beakers containing the active substance solution. Two beakers per concentration of active substance are used for the test. Then ground dog-biscuit is added to the beakers, which are covered with a copper gauze top.

Evaluation or mortality is made after 1, 2 and 5 days respectively. Subsequently, evaluation is made of the inhibiting action on pupation, metamorphosis, and shedding and emergence to the adult stage.

2-Cyclopropylamino-4,6-diamino-s-triazine and acid addition salts thereof have a good action in this test.

EXAMPLE 6

Test substances: 2-cyclopropylamino-4,6-diamino-s-triazine or an acid addition salt thereof formulated as 25% wettable powder or as aqueous solution or suspension of the hydrochlorides.

Test subject: *Lucilia sericata* (blowfly), freshly hatched larve I

Concentration: 250 ppm of active substance

Test method: 1 ml of an aqueous suspension or solution of the active substance in a concentration of 1000 ppm is added at 50° C. to 3 ml of a special culture medium so as to give a homogeneous mixture with an active substance content of 250 ppm. Approx. 30 Lucilia larvae are used for each test. Evaluation of mortality is made after 4 days.

In this test, 2-cyclopropylamino-4,6-diamino-s-triazine and acid addition salts thereof exhibit good action.

COMPARATIVE TESTS

Determination of the inhibition of development of insects

The following compounds have been tested:
I. 2,4-diamino-6-cyclopentylamino-s-triazine according to U.S. Pat. Nos. 2,909,421 and 2,567,847
II. 2,4-diamino-6-cyclohexylamino-s-triazine according to U.S. Pat. Nos. 2,909,421 and 2,914,508
III. 2,4-diamino-6-isopropylamino-s-triazine dihydrochloride according to U.S. Pat. Nos. 2,909,421 and 2,567,847
IV. 2,4-diamino-6-cyclopropylamino-s-triazine according to the present invention
V. 2,4-diamino-6-cyclopropylamino-s-triazine dihydrochloride according to the present invention

Test 1

Inhibition of the development of Musca domestica (order Diptera)

Test substance: 0.1% of test compound in acetone
Test subject: *Musca domestica*
Test material: nutrient substrate for maggots; preparation: in 9 l of water 100 g of yeast are suspended. The suspension is added to a mixture of 5 kg of bran/alfalfa (1:1). The material is then thoroughly mixed. After 5 days, the material is suitable for the test.

Concentration: 0.01% of test compound

Test method: amounts of 50 g of the nutrient substrate are charged into beakers (200 ml) of polyethylene. 5 ml of a 0.1% acetonic solution of the respective test compound is pipetted onto the nutrient substrate present in the beakers. The substrate is then thoroughly mixed and the acetone subsequently allowed to evaporate over a period of at least 20 hours. Then 25 eggs of Musca domestica are put into each of the beakers containing the treated nutrient substrate for testing of each test compound and also into beakers containing untreated nutrient substrate in the control group. Two beakers are used for each single test. After 5 days, the pupae are separated from the substrate by flushing them out with water and then deposited into beakers which are covered with a copper gauze top.

Valuation: After separation from the substrate, the numbers of normal and deformed pupae are counted. The number of flies which hatched out of the pupae is counted ten days after starting of the test.

Results:

| Compound No. | Pupae normal | Pupae deformed | Flies |
|---|---|---|---|
| I | 50 | 0 | 28 |
| II | 50 | 0 | 7 |
| III | 0 | 0 | 0 |
| IV | 0 | 0 | 0 |
| V | 0 | 0 | 0 |
| Control | 50 | 0 | 50 |

Test 2

Inhibition of the development of *Musca domestica* (order Diptera)

Test substance: 0.1% of test compound in acetone
Test subject: *Musca domestica*
Test material: nutrient substrate for maggots; preparation: in 9 l of water 100 g of yeast are suspended. The suspension is added to a mixture of 5 kg of bran/alfalfa (1:1). The material is then thoroughly mixed. After 5 days, the material is suitable for the test.

Concentration: 0.01% of test compound

Test method: amounts of 50 g of the nutrient substrate are charged into beakers (200 ml) of polyethylene. 5 ml of a 0.1% acetonic solution of the respective test compound is pipetted onto the nutrient substrate present in the beakers. The substrate is then thoroughly mixed and the acetone subsequently allowed to evaporate over a period of at least 20 hours. Then 25 maggots of Musca domestica are put into each of the beakers containing the treated nutrient substrate for testing of each test compound and also into beakers containing untreated nutrient substrate in the control group. Two beakers are used for each single test. After 5 days, the pupae are separated from the substrate by flushing them out with water and then deposited into beakers which are covered with a copper gauze top.

Valuation: After separation from the substrate, the numbers of normal and deformed pupae are counted. The number of flies which hatched out of the pupae is counted ten days after starting of the test.

Results:

| Compound No. | Pupae normal | Pupae deformed | Flies |
|---|---|---|---|
| I | 50 | 0 | 46 |
| II | 50 | 0 | 50 |
| III | 0 | 45 | 2 |
| IV | 0 | 45 | 0 |
| V | 0 | 45 | 0 |
| Control | 50 | 0 | 50 |

Test 3

Inhibition of the development of *Aedes aegypti* (order Diptera)

Test substance: 0.01% of test compound in acetone
Test subject: *Aedes aegypti*
Test material: tap-water
Concentration: 1 ppm of test compound
Test method: beakers (200 ml) of polyethylene are each filled with 150 ml of tap-water. Then 1.5 ml of a 0.01% solution of the respective test compound in acetone is pipetted onto the surface of the water. After the acetone has evaporated, 20 two-day-old larvae of *Aedes aegypti* are put into each of the beakers containing the test compound solution. Then ground dog-biscuit is added to the beakers, which are covered with a copper gauze top. Two beakers are used for each single test.

Valuation: The development of the larvae is observed periodically over a period of 10 days and the toxicity of the test compounds against the larvae (mortality in %) and the proportion of hatched mosquitos (% of adult mosquitos hatched) is determined.

Results:

| Compound No. | toxicity against larvae in % | hatched mosquitos in % |
|---|---|---|
| I | 25 | 75 |
| II | 0 | 100 |
| III | 0 | 100 |
| IV | 100 | 0 |
| V | 100 | 0 |
| Control | 0 | 100 |

Conclusion

The results given above show that a complete prevention of development of adult flies and mosquitos is achieved by treatment of eggs or larvae of the insects with compounds IV and V according to the present invention, which result is clearly not obtained with compounds I, II and III according to the prior art cited above.

What we claim is:

1. 2-Cyclopropylamino-4,6-diamino-s-triazine and acid addition salts thereof.

2. A pesticidal composition which comprises an effective pesticidal amount of 2-cyclopropylamino-4,6-diamino-s-triazine or an acid addition salt thereof together with a suitable carrier or additive or mixture thereof.

3. A method for combatting insects which comprises applying to their developmental stages an insecticidally effective amount of 2-cyclopropylamino-4,6-diamino-s-triazine or an acid addition salt thereof.

4. The method according to claim 3 for combatting insects in their larval or pupal stage in sufficient amount of inhibit metamorphosis.

5. The method according to claim 4 for combatting insects of the order Diptera.

6. The method according to claim 5 for combatting insects of the families Culicidae, Simuliidae, Tipulidae, Muscidae and Calliphoridae which belong to the order Diptera.

* * * * *